United States Patent
Licha et al.

(10) Patent No.: US 6,534,041 B1
(45) Date of Patent: Mar. 18, 2003

(54) ACID-LABILE AND ENZYMATICALLY DIVISIBLE DYE COMPOUNDS FOR DIAGNOSIS WITH NEAR INFRARED LIGHT AND FOR THERAPY

(75) Inventors: Kai Licha, Berlin (DE); Bjorn Riefke, Berlin (DE); Wolfhard Semmler, Berlin (DE); Wolfgang Wrasidlo, Berlin (DE)

(73) Assignee: Institute for Diagnostic Research GmbH of the Free University of Berlin, Berlin (DE)

( * ) Notice: Subject to any disclaimer, the term of this patent is extended or adjusted under 35 U.S.C. 154(b) by 0 days.

(21) Appl. No.: 09/403,418

(22) PCT Filed: Apr. 2, 1998

(86) PCT No.: PCT/DE98/01001

§ 371 (c)(1),
(2), (4) Date: May 1, 2000

(87) PCT Pub. No.: WO98/47538

PCT Pub. Date: Oct. 29, 1998

(30) Foreign Application Priority Data

Apr. 23, 1997 (DE) .......................... 197 17 904

(51) Int. Cl.$^7$ .............................. A61B 10/00
(52) U.S. Cl. ................. 424/9.6; 424/1.11; 424/1.65; 424/9.1
(58) Field of Search ................ 424/1.11, 1.49, 424/1.65, 9.1, 1.69, 9.3, 9.4, 9.5, 9.6, 9.7, 9.8; 558/300, 301, 302, 303; 430/616, 944

(56) References Cited

U.S. PATENT DOCUMENTS 6,083,485 A * 7/2000 Licha et al. .................. 424/9.6
6,140,494 A * 10/2000 Hamilton et al. .......... 536/26.6

FOREIGN PATENT DOCUMENTS

| EP | 0175617 | 3/1986 |
| EP | 0800831 | 10/1997 |
| WO | 0476408 | 3/1992 |
| WO | 9617628 | 6/1996 |
| WO | 9713490 | 4/1997 |
| WO | 9822146 | 5/1998 |

OTHER PUBLICATIONS

Licha, Kai et al.: "Synthesis and characterization of cyanine dye–poly(ethylene glycol) conjugates as contrast agents for in vivo fluorescence imaging" Proced. Spie–Int. soc. Opt. Eng., 1998, 3196, 98–102.

Patent abstracts of Japan, vol. 095, No. 009, Oct. 31, 1995 & JP 07 145148 Jun. 6, 1995.

Licha, K et al: "Synthesis and characterization of cyanine dyes as contrast agents for near–infrared imaging" Proced. Spie–Int. soc. Opt. Eng., 1996, 2927, 192–198.

* cited by examiner

Primary Examiner—Dameron L. Jones
(74) Attorney, Agent, or Firm—Millen, White, Zelano & Branigan, P.C.

(57) ABSTRACT

The invention relates to acid-labile and enzymatically divisible compounds for in-vivo and in-vitro diagnosis by means of near infrared radiation (NIR-radiation), the use of said compounds as optic diagnostic and therapeutic agents, and the diagnostic agents containing said compounds.

13 Claims, 6 Drawing Sheets

ACID-LABILE AND ENZYMATICALLY DIVISIBLE DYE COMPOUNDS FOR DIAGNOSIS WITH NEAR INFRARED LIGHT AND FOR THERAPY

This application is a 371 of PCT/DE98/01001 filed Apr. 2, 1998.

DESCRIPTION

The invention relates to acid-labile and enzymatically cleavable compounds for in-vivo and in-vitro diagnosis with near-infrared radiation (NIR radiation), the use of these compounds as optical diagnostic agents and therapeutic agents and diagnostic agents that contain these compounds.

Near-infrared imaging is a non-invasive diagnostic process, in which the high permeability of biological tissue to light on a wavelength 650–1000 nm is exploited. In contrast to the light of the ultraviolet and visible spectral range, which can penetrate only into the topmost millimeter of the tissue, penetration depths into the tissue of up to several centimeters is achieved with use of near-infrared light. The reasons for the basically small penetration depth of light are the absorption of endogenous dyes, mainly hemoglobin and water, which in the spectral range of the near-infrared light, however, have minimum values of between 650 and 1000 nm. This spectral range of the maximum optical tissue transparency is therefore also named a diagnostic/therapeutic window (Boulnois, J., Lasers Med Sci 1986, 1:47–66).

In addition to the modern imaging processes, such as diagnostic radiology, magnetic resonance tomography or ultrasonic diagnosis, another process for graphic tissue visualization is thus available to the diagnostician (Haller, E. B., Time-Resolved Transillumination and Optical Tomography. J. Biomed Optics 1996, 1:7–17).

The use of NIR radiation for site-dependent recording of blood flow and degree of oxygenation in the brains of babies by the detection of the absorption of hemoglobin/deoxyhemoglobin is a process that has been known and used for years (Jöbsis, F. F., Science 1977, 198: 1264–67; Chance, B.; Leigh, J. S.; Miyake, H. et al., Proc Natl Acad Sci USA 1988, 85: 4971–75; Benaron, D. A. et al., Science 1993, 33: 369A.).

The basic problem when near-infrared radiation is used is the strong scattering of light, so that even in the case of different photophysical properties, this object is poorly distinguished from an object with sharp edges and its surrounding area. The problem increases with increasing removal of the object from the surface and can be considered as a main limiting factor both in the case of transillumination and in the detection of fluorescence radiation. As contrast media, dyes, which mark the optical properties of the tissue and result in an increased absorption and fluorescence of the tissue that is to be detected, can therefore make unambiguous detection possible even with poor site resolution. In this case, the absorption behavior of such dye compounds can be used as imaging information. If the dyes, moreover, have the property of emitting the absorbed energy as fluorescence radiation, the latter can also be used as imaging information. In this case, the fluorescence radiation that is red-shifted relative to the excitation radiation is detected separately. The advantage exists, i.a., in that the tissue itself has an extremely low inherent fluorescence in the NIR range and thus the background is minimal. (S. Folli et al., Cancer Research 54, 2643–9 (1994); B. Ballou et al., Cancer Immunol. Immunother. 41, 257–63 (1995); X. Li et al., SPIE Vol. 2389, 789–98 (1995)).

In fluorescence diagnosis, the precondition in this respect is to detect an adequate difference that is as great as possible in the fluorescence emission between the tissue that is to be detected and the surrounding tissue. This can be achieved in principle by a difference in the concentration of the fluorescence dye at a certain time after the substance administration has been achieved. In particular for diagnosis in deeper tissue layers, this difference in the use of substances with unspecific concentration behavior is often inadequate.

The object of the invention is to make available new compounds that overcome the drawbacks of the prior art.

The object is achieved according to the invention by compounds of general formula (I)

$$(F—L)_m—A \qquad (I),$$

in which

F stands for a dye molecule with at least one absorption maximum of between 600 and 1200 nm, L stands for a linker structure, which contains an acid-labile and/or enzymatically cleavable bond, m is a number between 1 and 80, whereby if m is a number between 1 and 3, A represents a dye molecule with at least one absorption maximum of between 600 and 1200 nm, an antibiotically or anticytostatically active molecule, a biomolecule, a non-biological macromolecule or a compound B—(L—W)$_o$ or D—(L—W)$_o$, whereby D is a non-biological macromolecule, B is a biomolecule, L has the above-mentioned meaning, W represents an antibiotically or anticytostatically active molecule, o is a number between 1 and 20, and whereby if m is a number between 4 and 80, A represents a biomolecule, a non-biological macromolecule or a compound B—(L—W)$_o$ or D—(L—W)$_o$, whereby D, B, L, W and o have the above-mentioned meanings.

The special property with respect to the in-vivo detection of the near-infrared fluorescence emission of the compounds according to the invention consists in the fact that the latter have little or even no fluorescence emission, and an increase of the fluorescence signal occurs only after this construct is cleaved or after the dye is cleaved off from the construct on the target site (e.g., tumors, inflammations). The effective difference of the fluorescence signal between the tissue that is to be detected and the surrounding tissue is consequently marked by the fact of a) the concentration difference based on pharmacokinetics mechanisms and b) by the difference in the fluorescence quantum yield at the time of the diagnosis.

It has been found that the fluorescence of the dyes is quenched when a dye molecule is coupled to another molecule (dimer) while obtaining the compounds according to the invention, i.e., an extremely low fluorescence emission occurs in comparison to the corresponding dye molecule in the unbonded state. It has been found, moreover, that a comparable quenching occurs when other molecules with aromatic structures, which can be both dyes and active ingredients (e.g., cytostatic agents or antibiotic agents), are coupled with the fluorescence dye. Surprisingly enough, a quenching also occurs when the dyes are coupled to the antibodies, antibody fragments and proteins.

In principle, the dyes, which are structural components of the compounds according to the invention, must be distinguished in their monomeric unconjugated form by high molar absorption coefficients and high fluorescence quantum yields.

Preferred compounds of general formula I according to the invention are distinguished in that F and/or A stand for a polymethine dye, tetrapyrrole dye, tetraazapyrrole dye, xanthine dye, phenoxazine dye or phenothiazine dye.

Especially preferred are the structures from the class of polymethine dyes, since the latter have absorption maxima with very high molar absorption coefficients in the near-infrared spectral range of between 700 and 1000 nm (ξ up to 300,000 1 mol$^{-1}$ cm$^{-1}$), such as, for example, cyanine dyes, squarilium dyes and croconium dyes, as well as merocyanine and oxonol dyes.

Those compounds of general formula (I) according to the invention are also preferred in which F and/or A stand for a cyanine dye of general formula II (II)

in which

$R^1$ to $R^4$ and $R^7$ to $R^{10}$, independently of one another, stand for a fluorine, chlorine, bromine, iodine atom or a nitro group or for a radical —COOE$^1$, —CONE$^1$E$^2$, —NHCOE$^1$, —NHCONHE$^1$, —NE$^1$E$^2$, —OE$^1$, —OSO$_3$E$^1$, —SO$_3$E$^1$, —SO$_2$NHE$^1$, —E$^1$, whereby E$^1$ and E$^2$, independently of one another, stand for a hydrogen atom, a saturated or unsaturated, branched or straight-chain C$_1$–C$_{50}$ alkyl chain, whereby the chain or parts of this chain optionally can form one or more aromatic or saturated cyclic C$_5$–C$_6$ units or bicyclic C$_{10}$ units, and whereby the C$_1$–C$_{50}$ alkyl chain is interrupted by 0 to 15 oxygen atoms and/or 0 to 3 carbonyl groups and/or is substituted with 0 to 5 hydroxy groups, 0 to 5 ester groups, 0 to 3 carbon groups, 0 to 3 amino groups, and whereby in each case adjacent radicals R$_1$–R$_4$ and/or R$_7$–R$_{10}$ can be linked with one another with the formation of a six-membered aromatic carbon ring,

R$^5$ and R$^6$, independently of one another, stand for a radical —E$^1$ with the above-indicated meaning or for a C$_1$–C$_4$ sulfoalkyl chain, and/or R$^1$ to R$^{10}$ stand for a linkage with L, Q is a fragment oder in which R$^{11}$ stands for a hydrogen, fluorine, chlorine, bromine or iodine atom or a nitro group or a radical —NE$^1$E$^2$, —OE$^1$ or —E$^1$, whereby E$^1$ and E$^2$ have the above-indicated meaning or R$^{11}$ stands for a linkage with L, R$^{12}$ stands for a hydrogen atom or a radical E$^1$ with the above-indicated meaning, b means a number 0, 2 or 3, X and Y, independently of one another, represent O, S, —CH=CH— or a fragment $$\diagdown_C\diagup^{CH_2R^{13}}_{CH_2R^{14}}$$

in which

R$^{13}$ and R$^{14}$, independently of one another, stand for hydrogen a saturated or unsaturated, branched or straight-chain C$_1$–C$_{10}$ alkyl chain, which can be interrupted by up to 5 oxygen atoms and/or substituted with up to 5 hydroxy groups, and whereby radicals R$^{13}$ and R$^{14}$ can be linked with one another while forming a 5- or 6-membered ring.

Another subject of the invention are compounds of general formula (I), in which dyes with a therapeutically active molecule are linked via a physiologically cleavable bond, or dyes and active ingredients are coupled via physiologically cleavable bonds to biomolecules or non-biological carrier molecules.

Especially preferred are constructs, in which the fluorescence of the dye in the coupled state is quenched, and the therapeutic activity of the active molecule is masked by the coupling to the dye or carrier molecule (pro-drug effect). The cleavage of the bond results in an increase of fluorescence emission with simultaneous release of the activity of the active ingredient.

Active ingredients W and/or A in general formula (I) according to the invention are, for example, the compounds that are cited below:

Antibiotics: aclacinomycin, actinomycin F$_1$, anthramycin, azaserine, bleomycins, cactinomycin, carubicin, carzinophilin, chromomycins, dactinomycin, daunorubicin, doxorubicin, epirubicin, mitomycins, mycophenolic acid, nogalamycin, olivomycins, peplomycin, plicamycin, porfiromycin, puromycin, streptonigrin, tubercidin, zorubicin;

Folic acid analogs: denopterin, metothrexate, pteropterin, trimetrexate;

Pyridimidine analogs: ancitabine, azacitidine, 6-azauridine, carmofur, cytarabine, doxifluridine, enocitabine, floxuridine, 5-fluorouracil;

Purine analogs: fludarabine, 6-mercaptopurine, thiamiprine, thioguanine and derivatives of the above-mentioned compounds, Alkylating substances: alkylsulfonates, aziridines, ethylenimines, methylmelamines, nitroureas, nitrogen mustard compounds;

Hormonally active substances such as androgens, antiadrenals, antiandrogens, antiestrogens, estrogens, LH-RH analogs and progestogens, as well as other cytostatically active substances, such as taxol and taxol derivatives.

Other active ingredients are photodynamically active substances, which are distinguished by the capability, after excitation, to exert a photosensitizing action by forming cytotoxic singlet oxygen and radicals. Such compounds are primarily tetrapyrroles or tetraazapyrroles, for example porphyrins, benzoporphyrins, chlorines, purpurines, phthalocyanines, naphthalocyanines and derivatives of the above-mentioned compounds. Other compounds are expanded porphyrins, porphycenes and oxazine or phenoxazine dyes.

The chemical bond, which is contained in linker structure L according to general formula (I), is structurally constituted in such a way that the latter is cleaved in the case of certain physiological parameters that characterize diseased tissues (tumors) and that are distinguished from normal tissue areas.

It is described in the literature that tumors are characterized by low pH in comparison to the normal tissue. While the intracellular pH is largely identical (about pH 7.4), the extracellular pH in tumors is reduced to up to 0.5 pH units. Also, inflammations, especially of the bacterial type, are characterized by reduced pH. The methods for determining the pH are, i.a., measurements with microelectrodes, fluorescence measurements with pH-sensitive fluorescence samples and measurements with MR probes (R. J. Gillies et al., Am. J. Physiol. 267, pC 195–203 (1994), G. R. Martin and R. K. Jain, Microvascular Research 46, 216–230 (1993),

L. E. Gerweck and K. Seetharaman, Cancer Research 56, 1194–1198 (1996)),

K. Engin et al., Int. J. Hyperthermia 11 (1995) 211–216,

K. Engin et al., Int. J. Radiation Oncology Biol. Phys. 29 (1994) 125–132,

G. Helmlinger et al., Nature Medicine 3 (1997) 177–182.

Another subject of the invention are therefore compounds with linker structures L, which are cleaved by reduced physiological pH values. Such structures are, for example, alkylhydrazones, acylhydrazones, arylhydrazones, sulfonylhydrazones, imines, oximes, acetals, ketals, orthoesters corresponding to the fragments in which p stands for a number between 2 and 4.

In addition to the cleavage that is based on reduced pH, the cleavage of the compounds according to the invention can also be carried out by enzymes, which are present in increased concentration in the tissues that are to be detected (e.g., tumors, bacterial inflammations).

Another subject of the invention are therefore compounds with linker structures L, which can be cleaved enzymatically. Enzymatically cleavable linker structures are, for example, those that are cleaved by cathepsins, peptidases, carboxypeptidases, α-and β-glucosidases, lipasesi oxidases, phospholipases, phosphatases, phosphodiesterases, proteases, elastases, sulfatases, reductases, transferases and bacterial enzymes, for example penicillin-amidases as well as β-lactamases (P. D. Senter et al., Bioconjugates Chem. 6 (1995), 389–94).

Preferred enzymatically cleavable structures are short-chain peptide sequences, such as, for example, sequences that contain the amino acid sequence Val-Leu-Lys.

The kinetics that results in a concentration in the tissue that is to be detected or in a corresponding concentration gradient at a certain time after administration must correlate both with the kinetics of the cleavage of the compounds according to the invention and with the kinetics of the removal of the released dye molecule and result in a synergistic effect.

Other preferred compounds of general formula (I) according to the invention are distinguished in that A and/or B stands for an antibody, its conjugates and fragments, specific peptides and proteins, receptors, enzymes, enzyme substrates, nucleotides, natural or synthetic ribonucleic acids or deoxyribonucleic acids or their chemical modifications, such as aptamers or antisense oligonucleotides, lipoproteins, lectins, carbohydrates, mono-, di- or trisaccharides, linear or branched oligosaccharides or polysaccharides or -saccharide derivatives or for a dextran.

Also, the compounds of general formula (I) according to the invention are preferred in which D represents polyethylene glycol, polypropylene glycol, polylysine or polylysine dendrimers or derivatives thereof.

The linkage of structural elements A, D, B, L and W is carried out either directly or via commonly used functional groups. Such groups are, for example, esters, ethers, secondary and tertiary amines, amides, thiourea, urea, carbamate groups or maleimido structures.

Another subject of the invention is the use of the compounds of general formula I according to the invention for in-vivo diagnosis of diseased tissue areas with use of NIR radiation and for treatment of diseased tissue areas.

The subject of the invention is also an optical diagnostic agent for in-vivo diagnosis of diseased tissue areas with use of NIR radiation, which contains at least one compound of general formula (I) according to the invention.

These agents are produced according to the methods that are known to one skilled in the art, optionally with use of commonly used adjuvants and/or vehicles as well as diluents, etc. These include physiologically compatible electrolytes, buffers, detergents and substances for matching osmolarity as well as for improving stability and solubility. The measures that are commonly used in pharmaceutics ensure the sterility of the preparations during production and especially before administration.

The synthesis of dyes F and A is carried out according to methods that are known in the literature, e.g.

F. M. Hamer in *The Cyanine Dyes and Related Compounds*, John Wiley and Sons, New York, 1964;
J. Fabian et al., Chem. Rev. 92 (1992) 1197;
L. A. Ernst et al., Cytometrie [Cytometry] 10 (1989) 3–10;
P. L. Southwick et al., Cytometrie 11 (1990) 418–430;
R. B. Mujumdar et al., Bioconjugate Chem. 4 (1993) 105–11;
E. Terpetschnig et al., Anal. Biochem. 217 (1994) 197–204;
J. S. Lindsey et al., Tetrahedron 45 (1989) 4845–66, EP-0591820 A1;
L. Strekowski et al., J. Heterocycl. Chem. 33 (1996) 1685–1688;
S. R. Mujumdar et al., Bioconjugate Chem. 7 (1996) 356–362;
M. Lipowska et al., Synth. Commun. 23 (1993) 3087–94;
E. Terpetschnig et al., Anal. Chim. Acta 282 (1993) 633–641;
M. Matsuoka and T. Kitao, Dyes Pigm. 10 (1988) 13–22, and
N. Narayanan and G. Patronay, I. Org. Chem. 60 (1995) 2361–95.

The dyes are synthesized in a way similar to methods that are known in the literature with substituents that contain acid-labile or enzymatically cleavable bonds or from which such bonds are produced after coupling; e.g., according to B. M. Mueller et al., Bioconjugate Chem. 1 (1990) 325–330;
K. Srinivasachar and D. M. Neville, Biochemistry 28 (1989) 2501–09;
D. M. Neville et al., J. Biol. Chem. 264 (1989) 14653–61;
T. Kaneko et al., Bioconjugate Chem. 2 (1991), 133–41;
B. A. Froesch et al., Cancer Immunol. Immunother. 42 (1996), 55–63 and
J. V. Crivello et al., J. Polymer Sci: Part A: Polymer Chem. 34 (1996) 3091–3102.

The examples below explain the invention:

EXAMPLES

Figure 1:
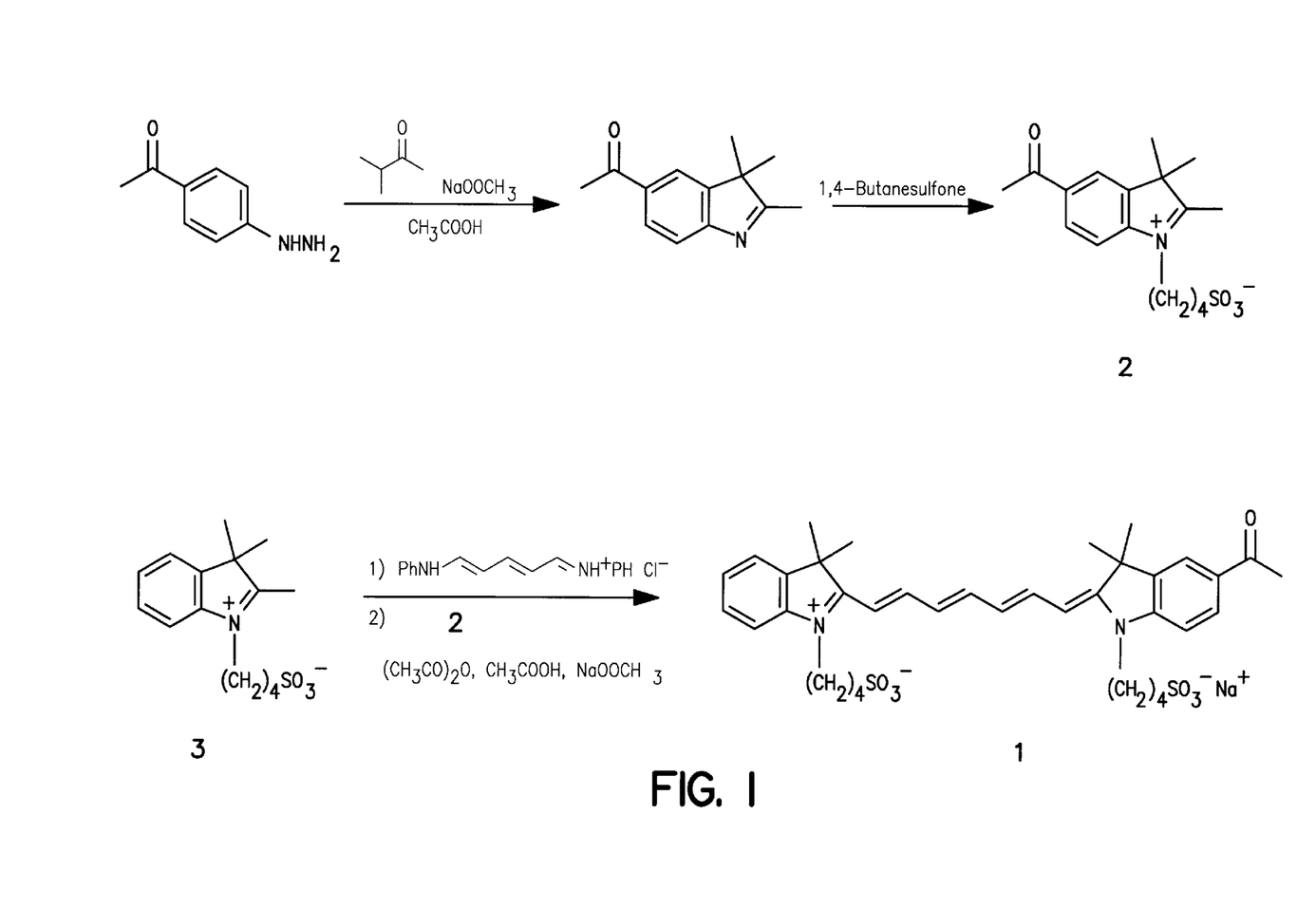
FIG. 1 shows the reaction scheme for the synthesis of 5-(1-Oxoethyl)-1,1'-(4-sulfobutyl)-indotricarbocyanine sodium salt.

1. Synthesis of 5-(1-oxoethyl)-1,1'-(4-sulfobutyl)-indotricarbocyanine-sodium salt 1 (FIG. 1)

4-Hydrazinophenylmethylketone is synthesized from 4-aminophenyl-methylketone by diazotization and reduction with $SnCl_2$ (in a way that is similar to T. Górecki et al., J. Heterocyclic Chem. 33 (1996) 1871–76).

4.8 g (32 mmol) of 4-hydrazinophenylmethylketone, 5.4 g of sodium acetate and 3.9 g (45 mmol) of 3-methyl-2-butanone are stirred in 40 ml of ethyl acetate for 1 hour at room temperature and for 4 hours at 120° C. The reaction mixture is concentrated by evaporation in a vacuum, taken up in 300 ml of dichloromethane, and the organic phase is washed with saturated NaCl solution. After drying on $MgSO_4$, 7.5 g of a brown oil is obtained. The latter is heated to 140° C. with 6.5 g (48 mmol) of 1,4-butanesulfone for 5 hours, stirred with acetone after cooling, and the precipitated solid is chromatographically purified (RP C-18, mobile solvent methanol/water). Yield: 2.5 g (23%) of 5-(1-oxoethyl)-1-(4-sulfobutyl)-2,3,3-trimethyl-3H-indolenine 2.

For production of dye 1, 0.5 g (1.7 mmol) of 1-(4-sulfobutyl)-2,3,3-trimethyl-3H-indolenine 3 is stirred with 0.47 g (1.6 mmol) of glutaconic aldehyde dianile hydrochloride in 10 ml of acetic acid anhydride for 30 minutes at 120° C. After cooling, it is mixed with 0.6 g (1.8 mmol) of 2, 10 ml of acetic acid anhydride, 4 ml of acetic acid and 0.5 g of sodium acetate, and it is heated for 30 minutes to 120° C. The dark blue solution is cooled, stirred with 200 ml of ether, and the precipitated solid is filtered off. After chromatographic purification (RP C-18, mobile solvent methanol/water) and freeze-drying, 0.3 g (26%) of product 1 is obtained.

Elementary analysis: Cld: C, 61.99; H, 6.33; N, 3.91; S, 8.95 Fnd: C, 61.73; H, 6.49; N, 3.80; S, 8.78.

Absorption: $\lambda_{max}$ ($H_2O$)=748 nm ($\xi$=14,800 l mol$^{-1}$ cm$^{-1}$)

Figure 2:
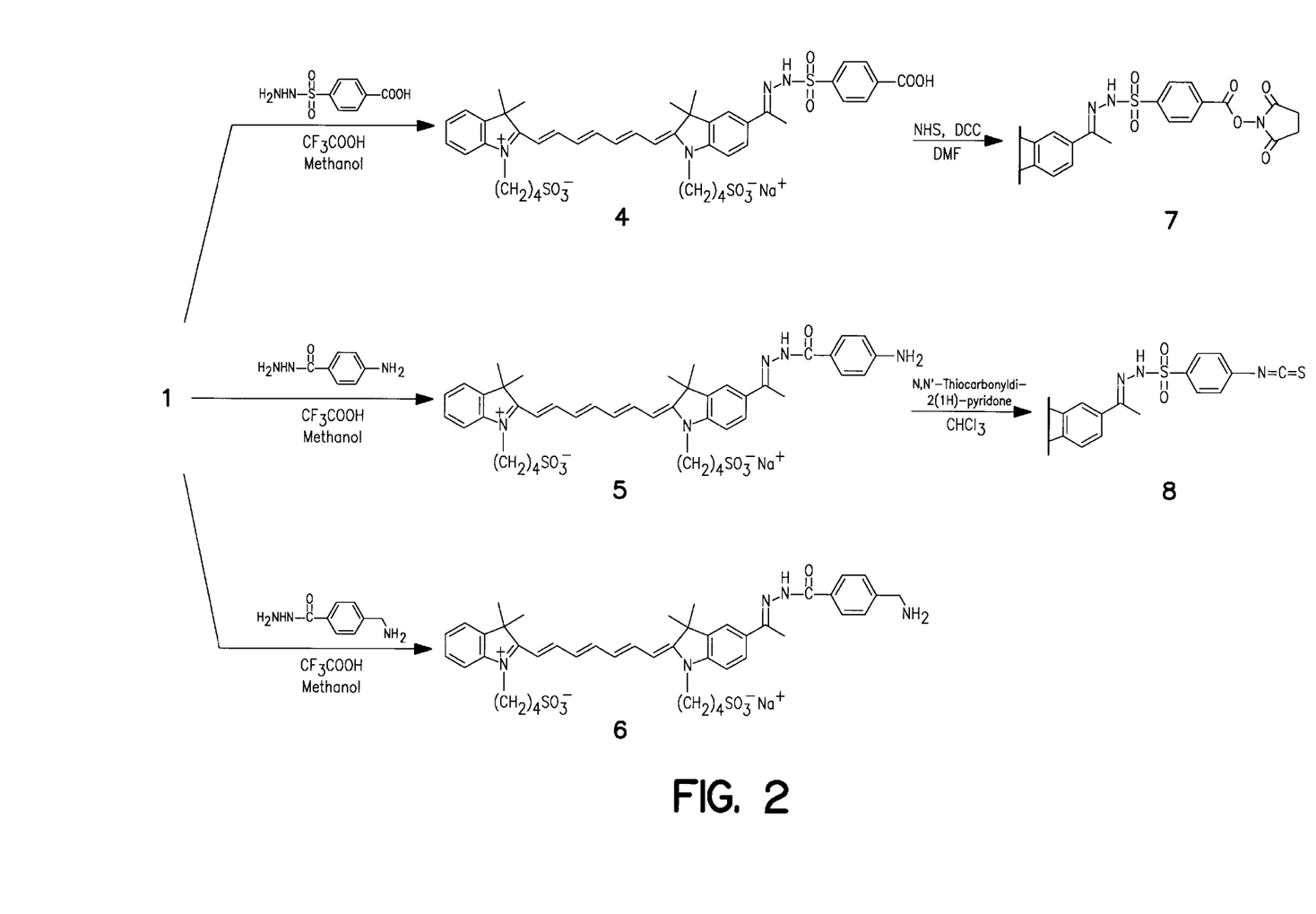
FIG. 2 shows the modification of the dye, from FIG. 1, with acid-labile linkers.

2. Modification with Acid-Labile Linkers (FIG. 2)

2.1 Reaction of 1 with 4-carboxyphenylsulfonylhydrazine 0.2 g (0.28 mmol) of 1 and 74 mg (0.34 mmol) of 4-carboxy-phenylsulfonylhydrazine are dissolved in 20 ml of methanol, mixed with 5 µl of trifluoroacetic acid and stirred for 18 hours at room temperature. The solvent is evaporated in a vacuum, the residue is washed several times with dichloromethane, and the product is dried. Yield: 0.21 g of 4.

2.2 Reaction of 1 with 4-aminobenzoic acid hydrazide 0.2 g (0.28 mmol) of 1 and 51 mg (0.34 mmol) of 4-aminobenzoic acid hydrazide are reacted analogously to 2.1. Yield: 0.20 g of 5.

2.3 Reaction of 1 with 4-(aminomethyl)benzoic acid-hydrazide 0.2 g (0.28 mmol) of 1 and 56 mg (0.34 mmol) of 4-aminomethylbenzoic acid hydrazide are reacted analogously to 2.1. Yield: 0.22 g of 6.

3. Production of Reactive Functional Groups (N-Hydroxysuccinimide Ester and Isothiocyanate) (FIG. 2)

For the production of corresponding N-hydroxysuccinimdiylester compound 7, 0.1 g (0.1 mmol)

of 4 with 14 mg (0.12 mmol) of N-hydroxysuccinimide (NHS) in 12 ml of dimethylformamide (DMF) is introduced and mixed at room temperature with a solution of 23 mg (0.11 mmol) of dicyclohexyl-carbodiimide in 1 ml of DMF. After 72 hours of stirring, the product is precipitated with diethyl ether, filtered off and reprecipitated from DMF/diethyl ether. The product that is obtained after vacuum drying (12 mg) is used without further purification.

For the production of acid-labile isothiocyanate compound 8, 0.1 g (0.11 mmol) of 5, 33 mg (0.14 mmol) of N,N'-thiocarbonyldi-2(1H)-pyridone and 15 mg (0.15 mmol) of triethylamine are stirred in 15 ml of chloroform for 60 minutes at room temperature. The product is precipitated with diethyl ether, filtered off and purified with use of HPLC (RP Select B, Merck, mobile solvent 10 mmol of phosphate buffer at pH 8/methanol). 40 mg (40%) of 8 is obtained after freeze-drying, separation of the salts with dichloromethane/methanol and drying in a vacuum.

4. Labeling of mAK 9.2.27 (Anti-Melanoma Antibodies)
4.1 Labeling with Acid-Labile NHS-Ester 7

1 mg of antibodies in 0.5 ml of 50 mmol of borate buffer (pH 9.2) is mixed with 33 $\mu$l of 7 (initial solution 5 mmol/l in DMF) and stirred for 1 hour at room temperature. Unbonded dye is separated via NAP-5 columns (elution with 25 mmol of phosphate buffer of pH 7.8, +0.01% NaN$_3$). The product mAK9.2.27/4-conjugate is stored in solution at 4° C.

Figure 5:
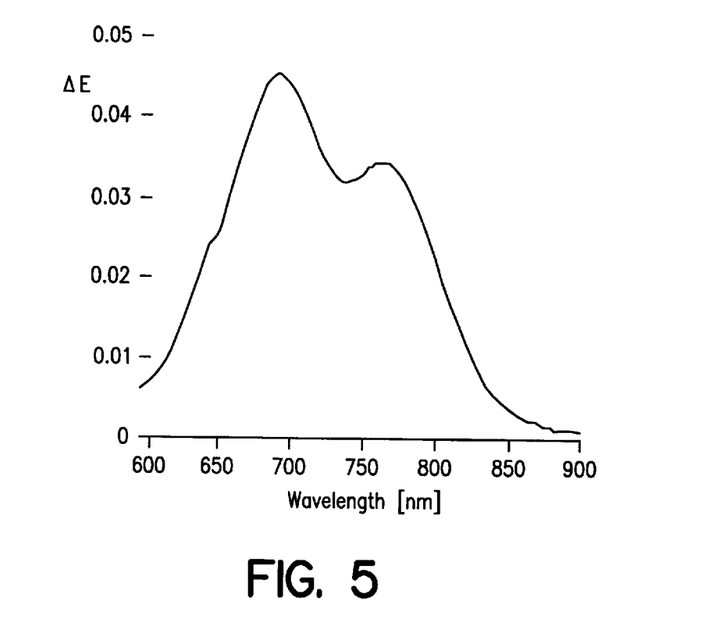
FIG. 5 shows the VIS/NIR absorption spectrum of mAK9.2.27/4-conjugate.

VIS/NIR absorption spectrum of mAK9.2.27/4-conjugate (in phosphate buffer at pH 7.8), see FIG. 5.

Fluorescence quantum yield Q=0.1% (5 $\mu$mol/l in phosphate buffer at pH 7.8; relative to indocyanine green as a standard with Q=13% in DMSO according to R. C. Benson and H. A. Kues, J. of Chemical and Engineering Data 22 (1977) 379).

4.2 Labeling with Acid-Labile Isothiocyanate 8

1 mg of antibodies in 0.5 ml of 50 mmol of borate buffer (pH 9.2) is mixed with 6 $\mu$l of 8 (initial solution 5 mmol/l in DMF) and stirred for 15 minutes at room temperature. Unbonded dye is separated via NAP-5 columns (elution with 25 mmol of phosphate buffer at pH 7.4, +0.01% NaN$_3$). The product mAK9.2.27/5-conjugate is stored in solution at 4° C.

Figure 3:
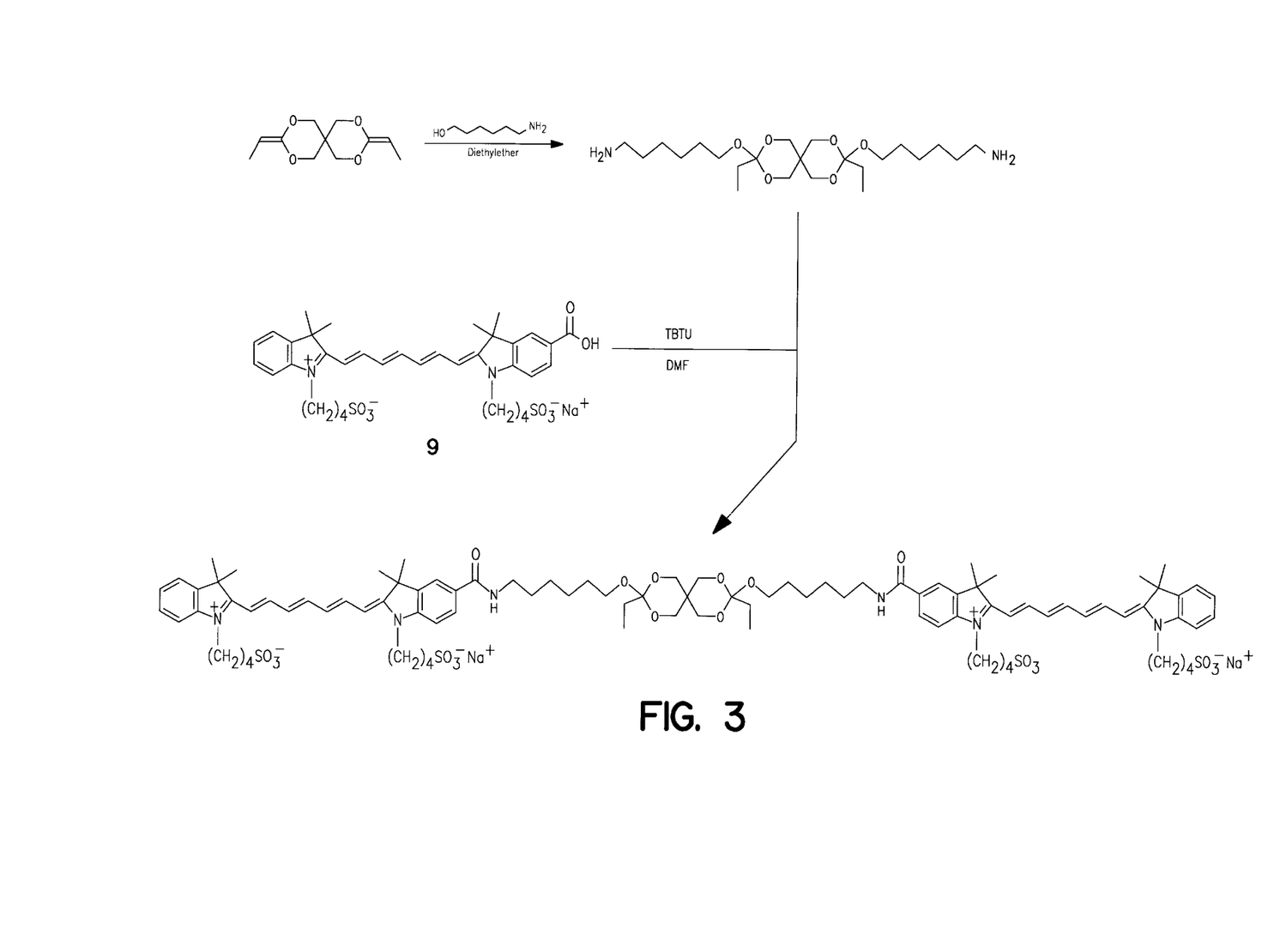
FIG. 3 shows the preparation of the symmetric spriodimer.

5. Synthesis of Dimeric Indotricarbocyanine Dyes
5.1 Production of Symmetrical Spiro Dimer 10 (FIG. 3)

0.1 g (0.47 mmol) of 3,9-diethylidene-2,4,8,10-tetraoxaspiro-[5.5]undecane (synthesized according to M. Crivello et al., J. Polymer Sci.: Part A: Polymer Chem. 34 (1996) 3091–3102) and 0.11 g (0.94 mmol) of 6-amino-1-hexanol are stirred in 15 ml of diethyl ether for 24 hours at room temperature, and the solvent is evaporated in a vacuum. The residue is dried on the oil pump and reacted without further purification.

0.2 g (0.28 mmol) of 5-carboxy-bis-1,1'-(4-sulfobutyl)-indotricarbocyanine-sodium salt 9 is, stirred in 15 ml of dichloromethane together with 0.09 g (0.28 mmol) of TBTU and 30 mg of triethylamine for 30 minutes and mixed with 0.06 g (0.14 mmol) of the above-mentioned Spiro compound in 2 ml of dichloromethane. After 18 hours of stirring at room temperature, the product is precipitated with diethyl ether and purified chromatographically (RP C-18, mobile solvent methanol/10 mmol of phosphate buffer at pH 8). After freeze-drying, the salts are precipitated with methanol/dichloromethane. 68 mg (26%) of product 10 is obtained.

Figure 6:
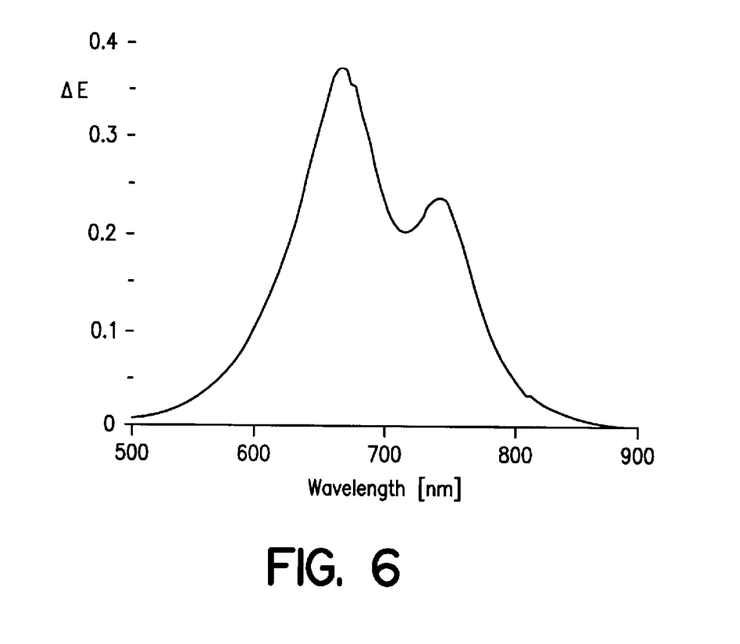
FIG. 6 shows the VIS/NIR absorption spectrum of the symmetrical spirodimer.

VIS/NIR absorption spectrum of 10 (5 $\mu$mol/l in phosphate buffer at pH 8), see FIG. 6.

Fluorescence quantum yield Q=0.2% (5 $\mu$mol/l in phosphate buffer at pH 8; relative to indocyanine green as a standard, see Example 4.1.).

Figure 4:
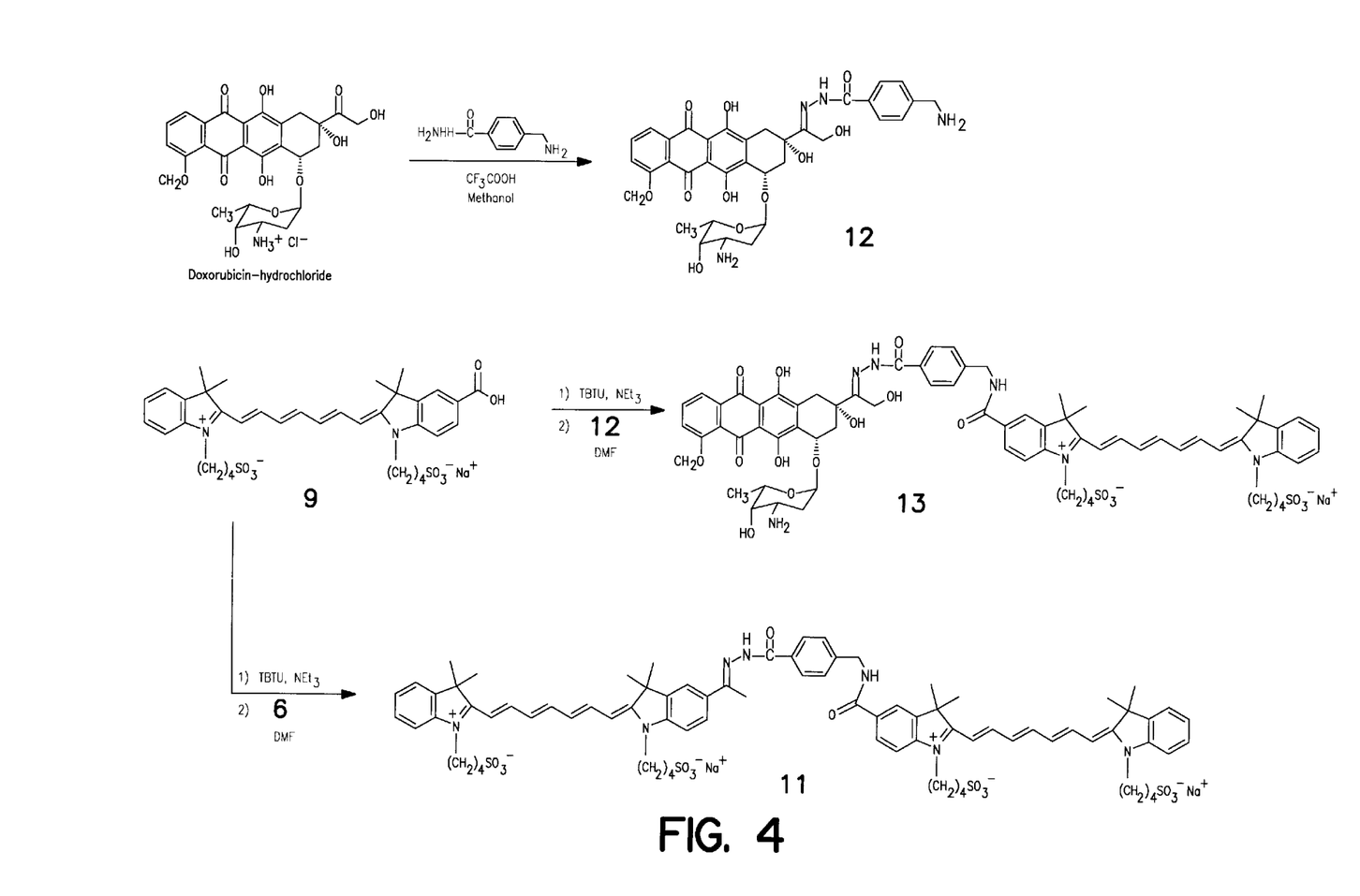
FIG. 4 shows the synthesis of a doxorubicin-indotricarbocyanine conjugate with an acid-labile linker.

5.2 Production of a Dye Dimer (11) with Acid-Labile Hydrazone Linkers of 6 (FIG. 4)

0.1 g (0.14 mmol) of 5-carboxy-bis-1,1'-(4-sulfobutyl)-indotricarbocyanine-sodium salt 9 is stirred in 10 ml of DMF together with 45 mg (0.14 mmol) of TBTU and 15 mg of triethylamine for 30 minutes and mixed with 0.14 g (0.16 mmol) of 6 in 2 ml of DMF. After 5 hours of stirring at room temperature, the product is crystallized out by adding diethyl ether, filtered off and chromatographically purified (RP C-18, mobile solvent methanol/10 mmol of phosphate buffer at pH 8). After freeze-drying, the salts are precipitated with methanol/dichloromethane. 0.13 g (59%) of 11 is obtained.

Figure 7:
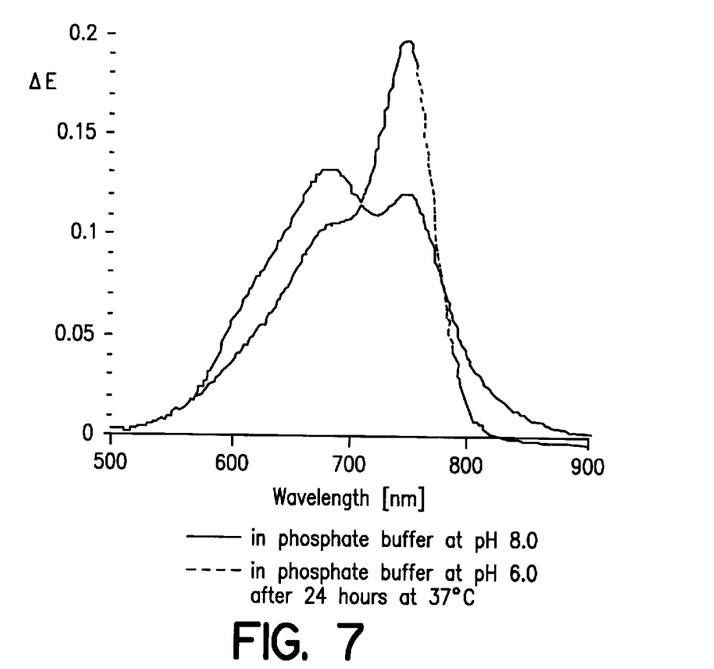
FIG. 7 shows the VIS/NIR absorption spectrum of a dye-dimer with an acid-labile hydrazone linker.

VIS/NIR-absorption spectrum of 11 (4 $\mu$mol/l) in phosphate buffer at pH 8.0 and in phosphate buffer at pH 6.0 after 24 hours at 37° C.; see FIG. 7.

6. Measurement of the Fluorescence Quantum Yield of 11 at Various pH Values as a Function of Time

Solutions of concentration 4 $\mu$mol/l in 50 mmol of phosphate buffer at pH values of 7.4; 7.0; 6.6; 6.0 and 5.0 are incubated at 37° C. At various times, aliquots are removed, and the fluorescence quantum yields are determined (SPEX Fluorolog Spectral fluorometer, 400 W Xe lamp, PM958 detector, calibrated with wave-length-dependent sensitivity of the detector, values related to indocyanine green, see Example 4.1.).

Figure 8:
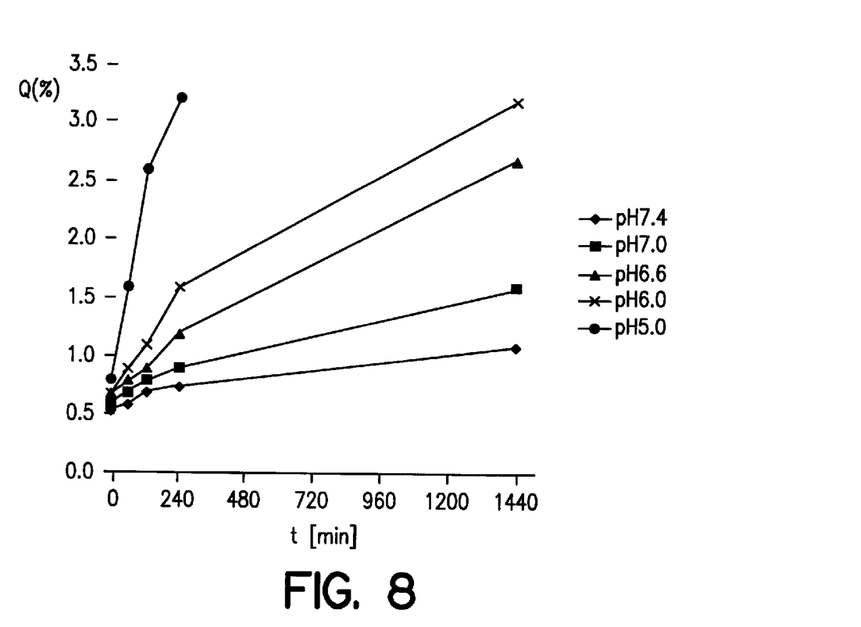
FIG. 8 shows the observation of the cleavage of the acid-labile dimer based on the increase in the fluorescence quantum yield at various pH values as a function of time.

The observation of the cleavage of acid-labile dimer 11 based on the increase in the fluorescence quantum yield in the case of various pH values as a function of time is shown in FIG. 8.

7. Synthesis of a Doxorubicin-Indotricarbocyanine Conjugate (13) with Acid-Labile Hydrazone Linkers (FIG. 4)

20 mg (34 $\mu$mol) of doxorubicin-hydrochloride and 11 mg (68 $\mu$mol) of 4-(aminomethyl)-benzoic acid hydrazide are stirred in 3 ml of anhydrous methanol after 2 $\mu$l of trifluoroacetic acid is added for 24 hours at room temperature. Product 12 is crystallized out with acetonitrile, centrifuged off, washed with acetonitrile and dried, yield 18 mg (24 $\mu$mol) of crude product. 14 mg (20 $\mu$mol) of 5-carboxy-bis-1,1'-(4-sulfobutyl)-indotricarbocyanine-sodium salt 9 is stirred in 0.5 ml of DMF together with 7 mg (22 $\mu$mol) of TBTU and 20 $\mu$l of triethylamine for 30 minutes. This reaction mixture is added drop by drop at 0° C. to a solution of above-mentioned 12 (18 mg of 0.2 ml of DMF) and stirred for 3 hours at 0° C. The product is precipitated by adding diethyl ether and chromatographically purified analogously to Example 5. 12 mg (47%) of 13 is obtained.

What is claimed is:
1. A compound of general formula I

$$(F-L)_m-A \qquad (I),$$

where
F is a cyanine, squarilium, croconium, merocyanine or oxonol dye molecule with at least one absorption maximum of between 600 and 1200 nm,
L is a linker structure which contains —C=N— and contains an acid-labile bond,
m is a number between 1 and 80,
whereby if m is a number between 1 and 3,
A is a dye molecule with at least one absorption maximum of between 600 and 1200 nm, an antibiotically or anticytostatically active molecule, a biomolecule, a non-biological macromolecule or a compound B—(L—W)$_o$ or D—(L—W)$_o$, whereby
D is a non-biological macromolecule,
B is a biomolecule,
L independently has the above-mentioned meaning, W is an antibiotically or anticytostatically active molecule, o is a number between 1 and 20, and whereby if m is number between 4 and 80,

A is a biomolecule, a non-biological macromolecule or a compound B—(L—W)$_o$ or D—(L—W)$_o$, whereby D, B, L, W and o have the above-mentioned meanings.

2. A compound according to claim 1, wherein A is a polymethine dye, tetrapyrrole dye, tetraazapyrrole dye, xanthine dye, phenoxazine dye or a phenothiazine dye.

3. A compound according to claim 1, wherein A is a cyanine, squarilium croconium, merocyanine or an oxonol dye.

4. A compound according to claim 1, wherein F and/or A is a cyanine dye of general formula (II)

(II)

in which

$R^1$ to $R^4$ and $R^7$ to $R^{10}$, independently of one another, is a fluorine, chlorine, bromine, iodine atom or a nitro group or for a radial —COOE$^1$, —CONE$^1$E$^2$, —NHCOE$^1$, —NHCONHE$^1$, —NE$^1$E$^2$, —OE$^1$, —OSO$_3$E$^1$—, —SO$_3$E$^1$—SO$_2$NHE$^1$, —E$^1$, whereby E$^1$ and E$^2$, independently of one another, represent a hydrogen atom, a saturated or unsaturated, branched or straight-chain C$_1$–C$_{50}$ alkyl chain, whereby the chain or parts of this chain optionally can form one or more aromatic or saturated cyclic C$_5$–C$_6$ units or bicyclic C$_{10}$ units, and whereby the C$_1$–C$_{50}$ alkyl chain is interrupted by 0 to 15 oxygen atoms and/or 0 to 3 carbonyl groups and/or is substituted with 0 to 5 hydroxy groups, 0 to 5 ester groups, 0 to 3 carboxy groups or 0 to 3 amino groups, and whereby in each case adjacent radicals R$^1$–R$^4$ and/or R$^7$–R$^{10}$ is optionally linked with one another with the formation of a six-membered aromatic ring,

R$^5$ and R$^6$, independently of one another, represent a radical

—E$^1$ with the above-indicated meaning or for C$_1$–C$_4$ sulfoalkyl chain, and/or R$^1$ to R$^{10}$ is a linkage with L Q is a fragment -continued in which

R$^{11}$ is a hydrogen, fluorine, chlorine, bromine or iodine atom or a nitro group or a radical —NE$^1$E$^2$, —OE$^1$, or —E$^1$, whereby E$^1$ and E$^2$ have the above-mentioned meaning or R$^{11}$ is a linkage with L, R$^{12}$ is a hydrogen atom or a radical E$^1$ with the above-indicated meaning, b is a number 0, 2, or 3, X and Y, independently of one another, represent radicals O, S, —CH=CH— or a fragment in which R$^{13}$ and R$^{14}$, independently of one another, is a hydrogen, a saturated or unsaturated, branched, or straight-chain C$_1$–C$_{10}$ alkyl chain, which can be interrupted by up to 5 oxygen atoms and/or substituted with up to 5 hydroxy groups, and whereby radicals R$^{13}$ and R$^{14}$ can be linked with one another while forming a 5- or 6-membered ring.

5. The compounds according to claim 1, wherein in general formula (I), W or A is an antibiotic, a folic acid, a pyrimidine, or a purine.

6. Compounds according to claim 1, wherein in general formula (I), L stands for a structure that contains an enzymatically cleavable chemical bond.

7. Compounds according to claim 1, wherein in general formula (I), L stands for a structure that is cleaved by cathepsins, peptidases, carboxypeptidases, α- and β-glycosidases, lipases, phospholipases, phosphatases, phosphodiesterases, proteases, elastases, sulfatases, reductases and bacterial enzymes.

8. A compound according to claim 1, wherein

A and/or B is an antibody, its conjugate or fragment, a specific peptide or protein, a receptor, an enzyme, an enzyme substrate, a nucleotide, a natural or synthetic ribonucleic acid, a deoxyribonucleic acid or its chemical modification such as a aptamer or a antisense oligonucleotide, a lipoprotein, a lectin, a carbohydrate, a mono-, di- or trisaccharide, a linear or branched oligosaccharide or a polysaccharide or -saccharide or a dextran.

9. The compounds according to claim 1, wherein in general formula (I), D is polyethylene glycol, polypropylene glycol, polylysine, or polylysine dendrimers.

10. A method for diagnosing diseased tissue, in vivo, comprising administering a compound according to claim 1 and near infrared radiation.

11. An optical diagnostic agent for in vivo diagnosis of diseased tissue with use of near infrared radiation, containing at least one compound according to claim 1 in combination with a pharmaceutically acceptable carrier.

12. A compound of general formula I (F—L)$_m$—A            (I), where F is a cyanine, squarilium, croconium, merocyanine or oxonol dye molecule with at least one absorption maximum of between 600 and 1200 nm L is a linker structure which contains —C=N— and contains an enzymatically cleavable bond, m is a number between 1 and 80, whereby if m is a number between 1 and 3,
- A is a dye molecule with a least one absorption maximum of between 600 and 1200 nm, an antibiotically or anticytostatically active molecule, a biomolecule, a non-biological macromolecule or a compound B—(L—W)$_o$ or D—(L—W)$_o$, whereby
- D is a non-biological macromolecule,
- B is a biomolecule,
- L independently has the above-mentioned meaning,
- W is an antibiotically or anticytostatically active molecule,
- o is a number between 1 and 20, and whereby if m is number between 4 and 80,
- A is a biomolecule, a non-biological macromolecule or a compound B—(L—W)$_o$ or D—(L—W)$_o$, whereby D, B, L, W and o have the above-mentioned meanings.

13. A method for treating diseased tissue, in vivo, comprising administering a compound according to claim 1 and near infrared radiation.

* * * * *